US007753247B2

(12) United States Patent
Pradel

(10) Patent No.: US 7,753,247 B2
(45) Date of Patent: Jul. 13, 2010

(54) SURGICAL STAPLING DEVICE

(75) Inventor: Christian Pradel, Kalefeld (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 0 days.

(21) Appl. No.: 12/016,628

(22) Filed: Jan. 18, 2008

(65) Prior Publication Data

US 2008/0179373 A1    Jul. 31, 2008

(51) Int. Cl.
*A61B 17/068* (2006.01)
(52) U.S. Cl. ............... 227/175.1; 227/176; 227/177.1; 227/19; 606/219
(58) Field of Classification Search ............ 227/175.1, 227/176.1, 19, 177.1; 606/219
See application file for complete search history.

(56) References Cited

U.S. PATENT DOCUMENTS

| 4,506,819 | A | * | 3/1985 | Rand | 227/120 |
| 5,100,041 | A | * | 3/1992 | Storace | 227/19 |
| 5,425,489 | A | * | 6/1995 | Shichman et al. | 227/108 |
| 5,427,299 | A | * | 6/1995 | Marks | 227/132 |
| 5,725,554 | A | * | 3/1998 | Simon et al. | 606/219 |
| 5,908,149 | A |   | 6/1999 | Welch et al. | |
| 5,938,101 | A | * | 8/1999 | Izuchukwu et al. | 227/176.1 |
| 6,450,391 | B1 | * | 9/2002 | Kayan et al. | 227/176.1 |
| 7,163,551 | B2 | * | 1/2007 | Anthony et al. | 606/219 |

FOREIGN PATENT DOCUMENTS

EP        0864297 A2    9/1998

OTHER PUBLICATIONS

International Search Report dated May 12, 2006 for PCT/EP2006/006822.

* cited by examiner

*Primary Examiner*—Rinaldi I. Rada
*Assistant Examiner*—Michelle Lopez
(74) *Attorney, Agent, or Firm*—Patent Central LLC; Stephan A. Pendorf

(57) ABSTRACT

A surgical stapling device for applying staples in a layer of tissue. A staple magazine is arranged in a device body and contains a plurality of spring loaded, stacked staples. A triggering element moves from a ready position to an actuation position causing an upper die to pick up a staple at an outlet of the staple magazine, to bend the staple feet inwards, and to fold, on an anvil engaging between the staple feet, the ends of a staple cross bar so as to form staple legs. A flat, spring-loaded tongue ejector element extends beneath the anvil. The ejector element is displaced against its direction of transport when the triggering element is moved from a readiness position into the actuation position, and is displaced in its direction of transport when the triggering element returns to the ready position so as to push the applied staple from the anvil.

8 Claims, 5 Drawing Sheets

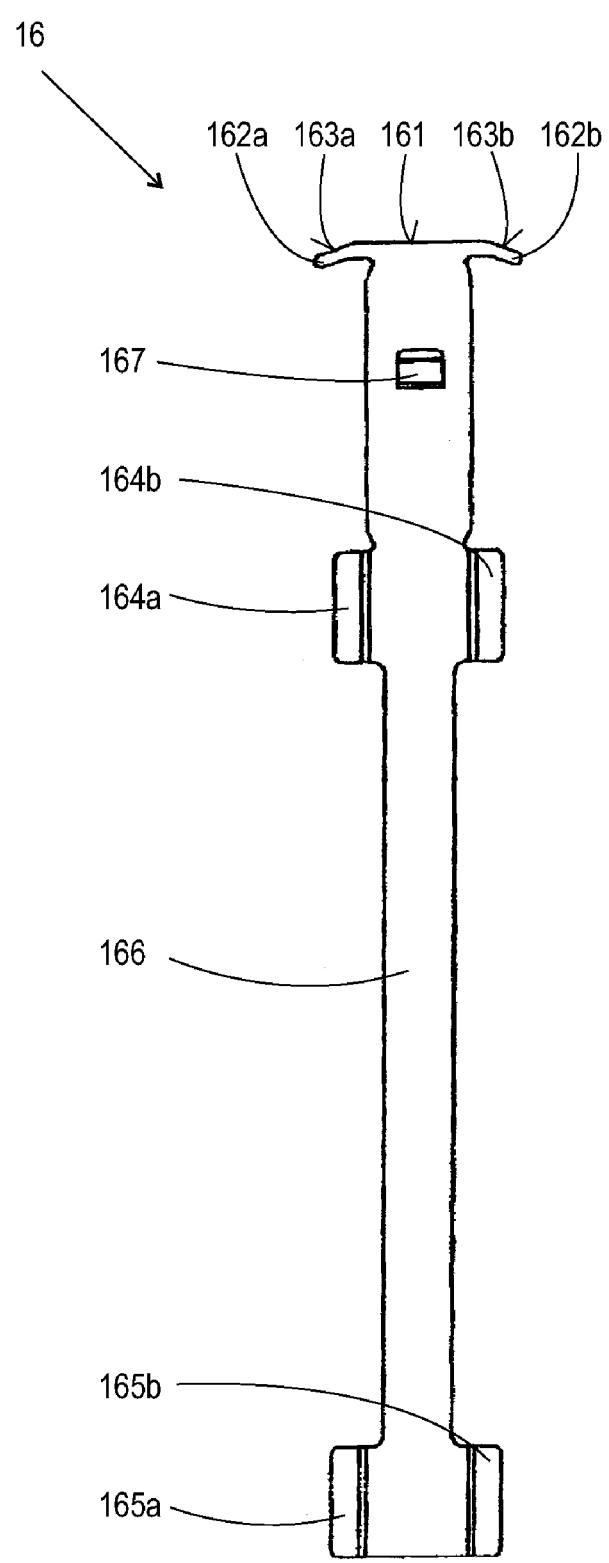
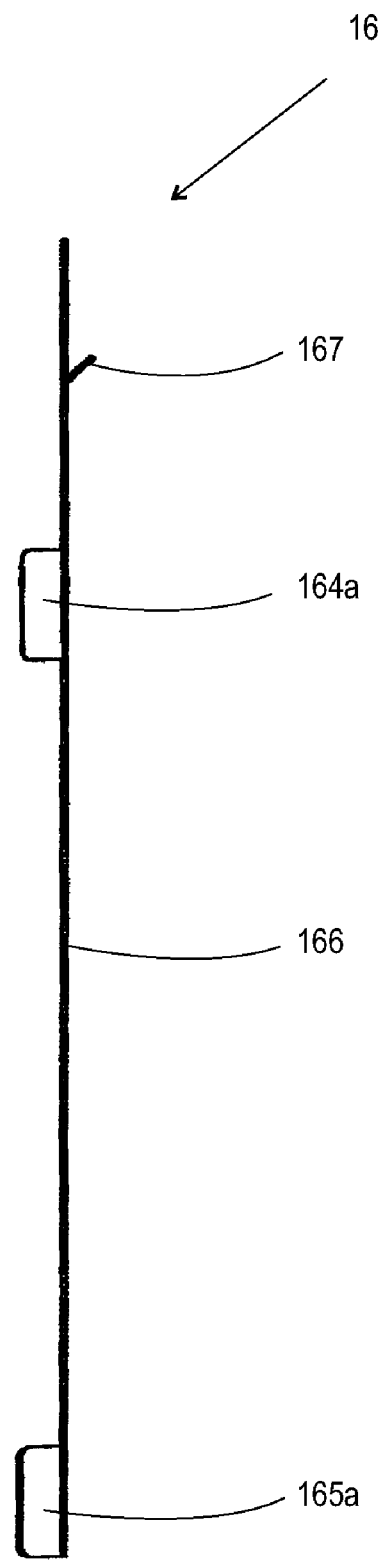
*Fig. 11*
*Fig. 12*

SURGICAL STAPLING DEVICE

CROSS-REFERENCE TO RELATED APPLICATIONS

This application is based upon and claims priority from prior International Application No. PCT/EP2006/006822 filed on 12 Jul. 2006, which claims priority from German Patent Application 10 2005 034 516.6 filed on 20 Jul. 2005, the entire disclosures of which are hereby incorporated herein by reference.

BACKGROUND OF THE INVENTION

1. Field of the Invention

The present invention generally relates to the field of surgical stapling devices, and more particularly to a surgical stapling device for applying staples in a layer of tissue.

2. Description of Related Art

A generic surgical stapling device is marketed under the name "Leukoclip" by the firm Smith & Nephew Medical Ltd., Hull, Great Britain. The Leukoclip comprises a handle-shaped device body to which is pivotably attached a similarly handle-shaped triggering lever. The triggering lever is connected to a mechanism that engages in a housing part that can be slid onto the device body. In its lower area the slide-on housing part contains a linear staple magazine and in its upper part it has a slide element, referred to as the upper die, and a guide therefore.

In the staple magazine are stacked a plurality of staples, one behind each other, in a pre-application position. In the pre-application position each staple consists of a straight staple cross bar with staple feet bent laterally and substantially perpendicular thereto. The staple feet have pointed ends. The entire stack of staples is spring-loaded in the staple magazine so that the stack of staples is forced towards a staple outlet of the magazine. Each foremost staple in the stack of staples is positioned directly under the upper die. When the triggering lever is actuated, its mechanism pushes the upper die downwards, against spring pretension, towards the staple outlet. There, a groove in the front edge of the upper die and running parallel to the staple outlet, receives the staple cross bar of the foremost staple and transfers the foremost staple to an anvil below the staple outlet. The anvil consists of a metal tab that is fixed relative to the staple outlet and is oriented parallel and centrally to the staple cross bar, extending approximately over half the width of the staple cross bar. When the triggering element is further actuated, the staple crossbar is pressed by the front edge of the upper die against the anvil, while side areas of the upper die, which are movable relative to this front edge, fold downwards the two outer sections of the staple cross bar extending laterally beyond the anvil and thus bend the staple feet inwards. The folded areas between the staple feet and the remaining staple cross bar are referred to in this case as staple legs. When the Leukoclip is used as intended, the pointed staple feet penetrate into a layer of tissue and are secured in position when bent. In this way, the edges of a wound, for example, can be held in an abutting position to each other.

In order to support detachment of the applied staple from the Leukoclip stapling device, a "kick-off" mechanism is provided beneath the staple magazine. This mechanism takes the form of a flat metal tongue that extends to a point directly below the anvil. It can be displaced linearly and is spring-loaded against the direction of staple transport in the magazine. This means that in the relaxed state the front edge of the kick-off tongue is located behind the front edge of the anvil, while in the tensioned state both front edges are flush with one another. An extension of the kick-off tongue, designed as a separate push rod, extends through the rear wall of the slide-on device part so that in the assembled state of the Leukoclip stapling device, and with the triggering lever in the ready position, the kick-off tongue extension is displaced forwards against the spring pressure into the tensioned position by a corresponding shoulder on the triggering lever, i.e. the front edge of the tongue comes flush with the anvil.

When the triggering lever is actuated, the kick-off tongue extension is released, the tensioning spring relaxes and the kick-off tongue is displaced rearwards as the staple is being applied. Only when the triggering lever has been released, i.e. it has returned to its ready position after application of the staple, does the kick-off tongue return to its tensioned position, in which it exerts pressure from behind with its front edge against the folded staple legs and thus actively detaches the applied staple from the anvil.

What is disadvantageous in this known stapling device is the fact that a large degree of mechanical effort must be put into the design of the kick-off mechanism. In order to tension the spring against the staple transport direction a spiral spring must be used as an additional component, and at least one rigid projection passing through the tongue must be created as an abutment for the spiral spring, so that the direction of the spring tension can be reversed. In addition, in the Leukoclip the tongue extension takes the form of a separate push rod, which requires the use of an additional component with corresponding manufacturing and assembly costs.

EP 0 864 297 A2 and the parallel U.S. Pat. No. 5,908,149 A describe a surgical stapling device that is commercially available under the name "Proximate Plus MD" and has a simplified kick-off mechanism. In this stapling device, a kick-off tongue is arranged beneath the anvil and its front area can be bent elastically downwards. When the staple is applied, the folding of the staple legs, which interact with the rounded end areas of the front edge of the kick-off tongue, cause the front area of the tongue to bend elastically downwards. When the triggering lever is returned to its ready position, the downward-bent front area of the tongue snaps back into its starting position at the moment when the guiding groove of the upper die releases the staple cross bar and, as it moves upwards, comes into contact with the rear surfaces of the bent staple legs, thereby pushing the entire staple off the anvil.

One disadvantage of this device is the rapid wear that occurs to the plastic kick-off tongue, in particular in the lateral end areas of the front edge of the tongue, which are particularly important for the action and which are heavily stressed when the device is actuated. Even slight wear in this area results in the tip of the tongue no longer being sufficiently bent downwards and the ejection force is correspondingly reduced when the tip snaps back. Another disadvantage of this device is that when the kick-off tongue is bent downwards, it can come into contact with the tissue to be stapled and this can give rise to undesired contamination.

SUMMARY OF THE INVENTION

It is the purpose of the present invention to provide a kick-off mechanism for a generic stapling device or for a retrofittable ejector element that is mechanically simpler and cheaper in design.

The invention relates to a surgical stapling device for applying staples in a layer of tissue, comprising
  a device body
  a staple magazine arranged in the device body and in which
    are stacked a plurality of staples, each in a pre-application position and having a staple cross bar and laterally connected thereto two substantially vertically bent staple feet, with the stack of staples being spring loaded in a staple transport direction towards a staple outlet from the magazine, a triggering element that, when it is moved from a ready position to an actuation position, causes an upper die to pick up a foremost staple at the outlet of the staple magazine and to bend the staple feet inwards into an application position, after folding at either end of the staple cross bar a section so that it becomes a staple leg, on an anvil engaging between the staple feet, said anvil acting as an abutment for the staple cross bar, an ejector element having a front edge and designed as a flat, spring-loaded tongue extending beneath the anvil centrally and parallel to the direction of transport, and being linearly movable in its direction of extension, the ejector element, when the triggering element is moved from the readiness position into the actuation position, being displaced against the direction of transport and, when the triggering element is returned to the ready position, being displaced in the direction of transport, pushing the applied staple from the anvil.

The invention further relates to an ejector element for a surgical stapling device of this type.

In contrast to the present state of the art, the ejector element according to the invention, i.e. the kick-off tongue according to the invention, is spring-loaded in the direction of transport of the staples. In this way, it is possible to dispense with a complicated mechanism to reverse the spring force and to actively actuate the kick-off spring. This substantial mechanical simplification is made possible by providing the front end of the ejector element with a special shape. According to the invention, the ejector element has the shape of an arrowhead, in which the front edges of the wings of the arrowhead slant obliquely backwards. In this way it is ensured that the obliquely backward-slanting edges of the arrowhead wings interact with the inner and rear sides of the staple legs when the latter are being folded, and act as sloping planes. As the staple legs are further folded, the distance between them narrows, so that the kick-off tongue is displaced to the rear against the spring loading, and the front edges of the arrowhead wings slide along the inner and rear surfaces of the staple legs. As a result, force acts upon the staple to be applied, in the direction of transport of the staples, as the staple legs are undergoing folding. However, the staple remains positioned on the anvil, because the staple cross bar is held there by the upper die. The moment when the upper die releases the staple cross bar, i.e. when the triggering lever returns to its ready position, is the moment when the staple, which is by then applied, ceases to be held in position, so that the spring preloading on the kick-off tongue is relaxed and the applied staple is actively pushed off the anvil. In the process, the tip of the kick-off tongue executes a purely linear motion, so that there is no need to fear any risk of contamination, for example, by the tip of the tongue being bent downwards.

It is particularly favorable if the front edge of the arrowhead is broader than the distance between the staple legs in their application position. This way a complete division of tasks between the front edge and the wings of the arrowhead is achieved: while the arrowhead wings are solely responsible for returning the ejector element and thus for building up the spring tension, the active pushing of the applied clip off the anvil is a task reserved for the front edge.

It is particularly advantageous if an elastically resilient area is provided in a rear section of the ejector element. This makes it unnecessary to use a separate spring element to apply the spring force.

In a particularly favourable embodiment of the invention this rear area is designed as a bending spring that flexes perpendicularly to the direction of extension of the ejector element. This can be accomplished, for example, by tapering an area of an ejector element that is designed as a metal tongue. This is mechanically particularly easy to achieve because no substantial structural changes are required in the elastically resilient section.

Preferably, the linear motion of the ejector element against the direction of transport is limited by a stop in the device body. This stop serves as an abutment for the spring force that is to be built up. Without such a stop, there would be a risk that the ejector element would be displaced rearwards, because of its arrowhead shape, while the staple is being applied, but no spring force would be built up.

Advantageously, the ejector element possesses lateral guide fins for mounting it in a linearly movable manner in corresponding guide recesses in the device body. The guide fins ensure the purely linear motion of the overall ejector element. Only the elastically resilient part, when designed as a bending spring, can deform slightly in a perpendicular direction to this linear motion.

The guide fins are arranged preferably in pairs in front of and behind the elastically resilient area of the ejector element, particularly advantageously at the shortest possible distance from said area. As a result, the area of the ejector element that is deformed perpendicularly to the direction of the spring force, and thus also the amount of spring force that is built up, are precisely defined.

A further refinement of the invention that serves to bring about this effect is the fact that the guide fins are advantageously angled with a component perpendicular to the direction of extension of the ejector element. This results in greater rigidity of the kick-off tongue in the areas outside the elastically resilient area.

In an advantageous embodiment of the invention, the ejector element has a safety projection that limits its movement in the direction of transport by interacting with a corresponding stop in the device body. This stop secures the ejector element against slipping out of its mounting in the direction of transport of the staples. The corresponding safety projection can be particularly advantageously designed as a tab arranged at an angle with a component perpendicular to the direction of extension. Such a tab can easily be produced by stamping techniques. Alternatively, a through-opening, e.g. a longitudinal hole, can also be provided in the kick-off tongue, with a corresponding bolt in the device body passing through it to fulfill the function of the stop.

BRIEF DESCRIPTION OF THE DRAWINGS

Further advantages and features of the invention are apparent from the following specific description and the associated Figures, which show:

FIG. 11 illustrates a top view of an ejector element according to one embodiment the invention.

FIG. 12 illustrates a side view of the ejector element shown in FIG. 11.

DETAILED DESCRIPTION

Figure 1:
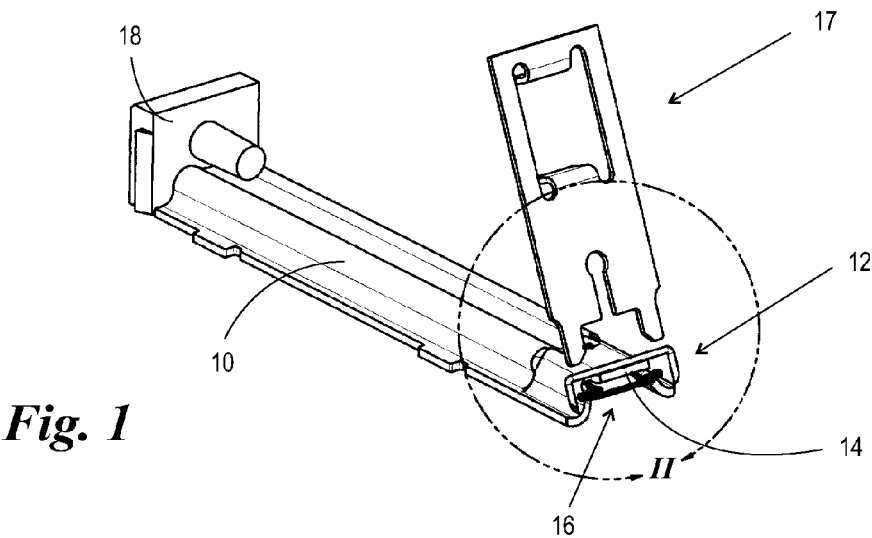
FIG. 1 illustrates a perspective view of the staple ejection area of a stapling device according to one embodiment of the invention in a ready position.
Figure 2:
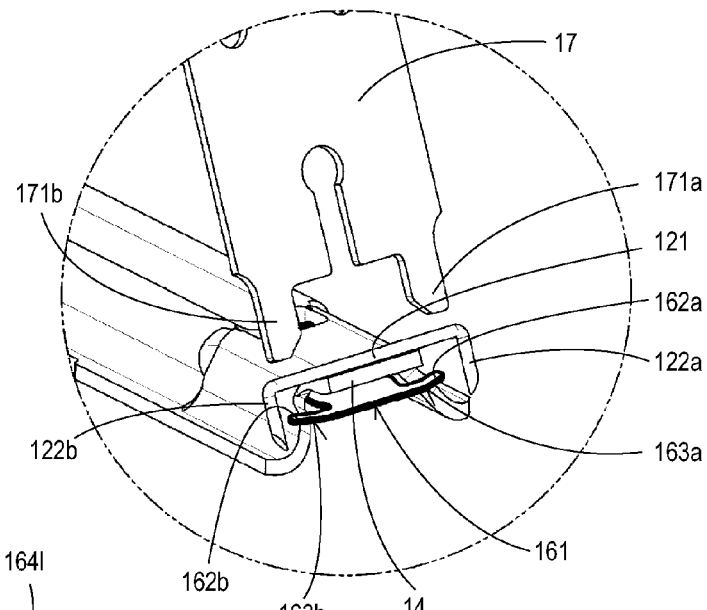
FIG. 2 illustrates an enlarged view of a section of FIG. 1.
Figure 3:
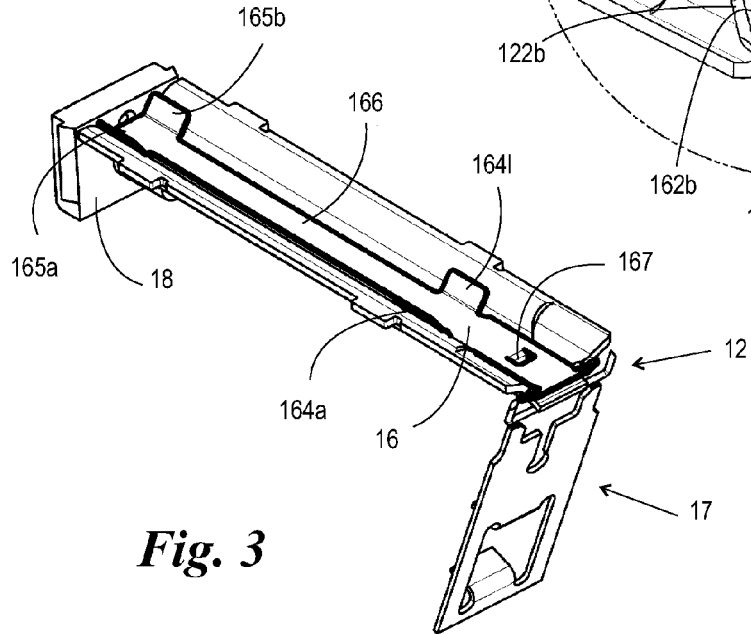
FIG. 3 illustrates a bottom view of the object shown in FIG. 1.
Figure 4:
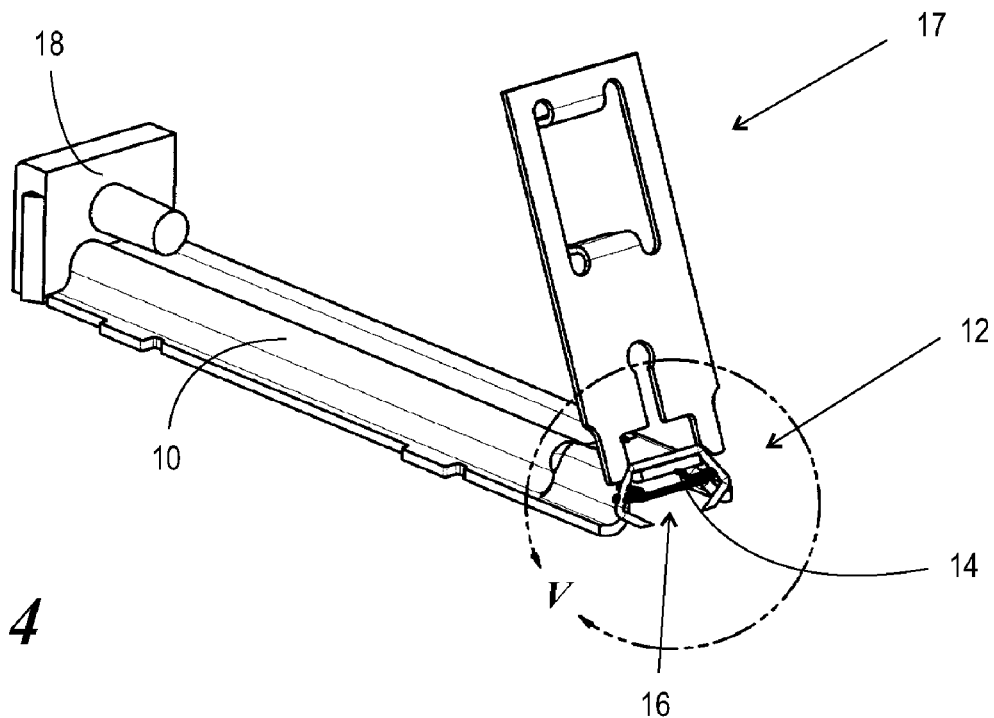
FIG. 4 illustrates a perspective view of the staple ejection area of the stapling device according to one embodiment of the invention in an intermediate position while the staple legs are being folded.
Figure 5:
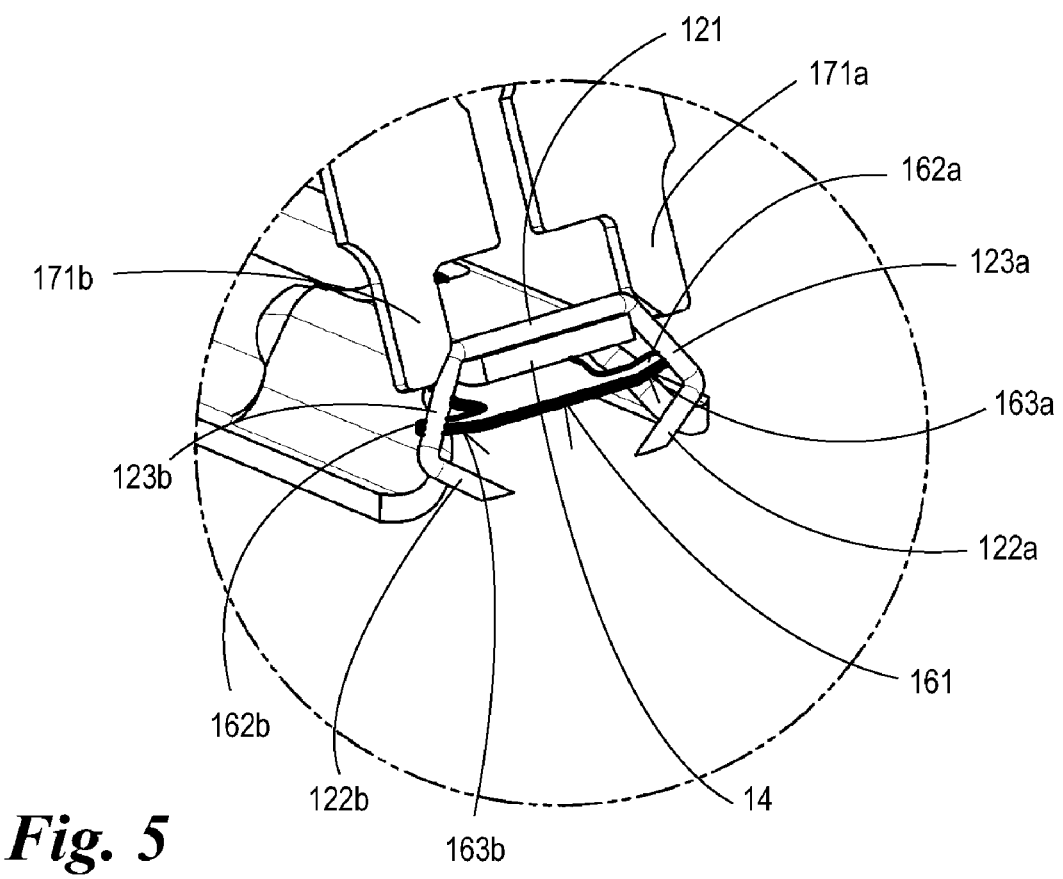
FIG. 5 illustrates an enlarged view of a section of FIG. 4.
Figure 6:
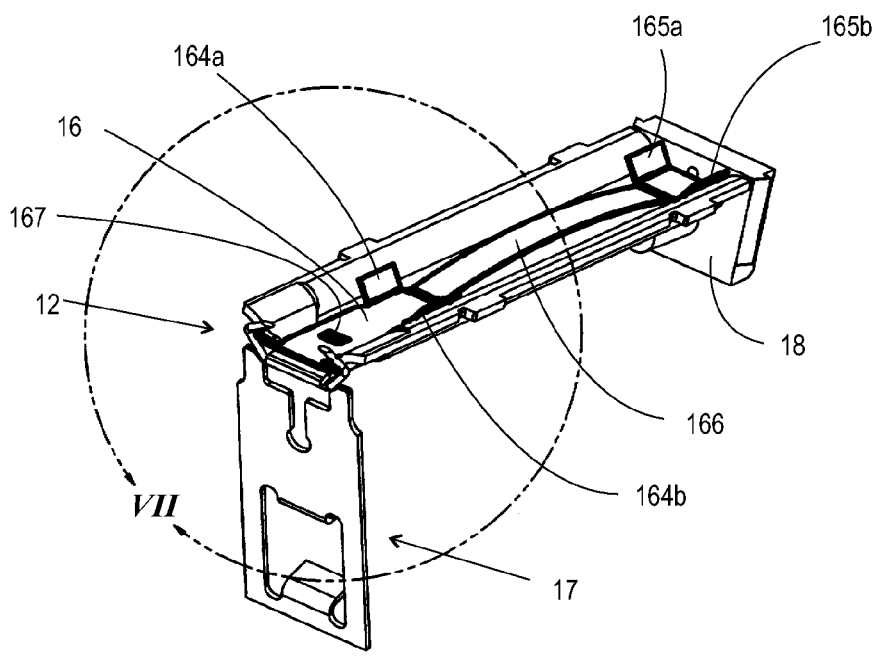
FIG. 6 illustrates a bottom view of the object shown in FIG. 4.
Figure 7:
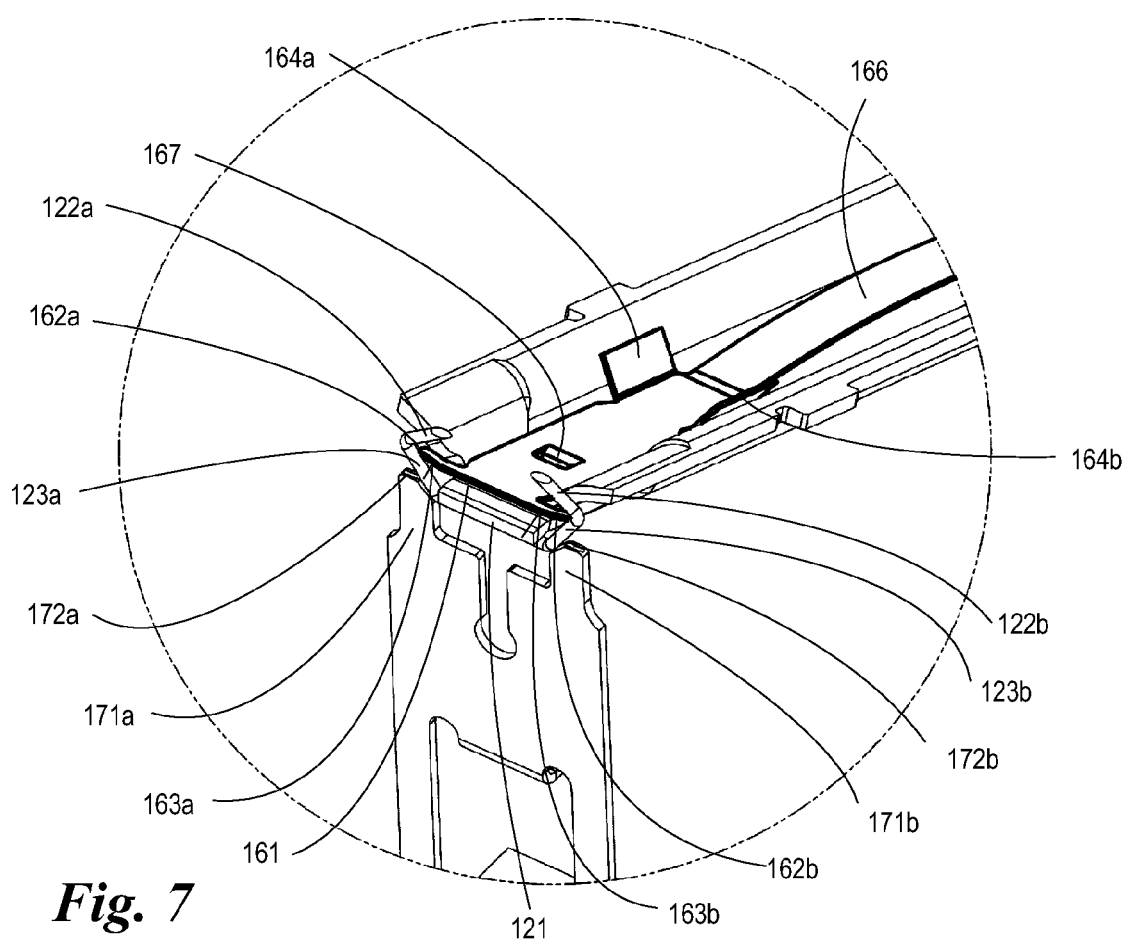
FIG. 7 illustrates an enlarged view of a section of FIG. 6.

FIGS. 1-10 show the ejection mechanism of the stapling device according to the invention in various stages of the staple application process. Only the individual parts relevant to the description of the invention are shown therein. Identical parts in the Figures are given the same reference numbers. A guide frame 10, on which normally a batch of staples 12 is slidingly supported, is shown as part of the staple magazine. For the sake of clarity, only the staple 12 closest to the outlet of the magazine is shown in FIG. 1. FIGS. 1 to 3 illustrate a ready position. As can be seen from FIG. 2, the staple, in its pre-application position, consists of a staple cross bar 121 and two staple feet 122a and 122b folded substantially at right angles thereto and having pointed ends. In this pre-application position the staple cross bar 121 rests on a projection of the guide frame which is referred to as an anvil 14. In the embodiment shown, the anvil 14 is angled slightly upwards against the rest of the guide frame 10. The front area of a tongue-like ejector element 16 projects forward beneath the anvil. The entire ejector element 16 is very clearly visible in the bottom view shown in FIG. 3. The front edge of said ejector element is shaped like an arrowhead, with a flat front edge 161 merging into lateral wings 162a and 162b of the arrowhead, which in turn possess front edges 163a and 163b that slope towards the rear. The ejector element in addition has two pairs of guide fins 164a and 164b or 165a and 165b. The guide fins take the form of obliquely sloping lateral projections of the ejector element. Between the pairs of guide fins 164a, 164b and 165a, 165b there is arranged an elastically resilient area 166 of the ejector element 16. The elastically resilient area 166 is created by a lateral tapering of the otherwise tongue-shaped ejector element.

Furthermore, between its front area and the first pair of guide fins 164a, 164b, the ejector element 16 is provided with a tab 167 angled towards the inside of the guide frame 10, said tab acting as a safety projection and interacting with a corresponding stop element, which is not shown in further detail here, to prevent the ejector element from sliding out of its guided position. The tab 167 can be seen in particular in the separate depiction of the ejector element 16 in FIGS. 11 and 12.

In FIGS. 1 to 3 one can also see a flat element, referred to as an upper die 17, that can be moved via a mechanism, which is not depicted here, by actuating a triggering element, which is also not illustrated here. In its front area the upper die has two bevelled projections 171a and 171b, the distance between which is slightly larger than the width of the anvil 14.

FIGS. 4 to 7 show an intermediate stage in the actuation of the stapling device according to the invention. Through the actuation of a triggering device that is not shown in the Figures, the upper die 17 is moved downwards by means of a mechanism, which is also not shown, onto the staple 12 waiting in the pre-application position. In the process, the bevelled projections 171a, 171b interact with the lateral end areas of the staple cross bar 121. In order to improve the holding of the staple 12 on the anvil 14, the inner edges of the projections 171a, 171b are provided with grooves 172a, 172b. As the upper die is advanced, the lateral marginal areas of the staple cross bar 121 are folded downwards and thus form staple legs 123a, 123b. Next, the staple feet 122a, 122b are bent downwards. When this takes place, the pointed tips of the staple feet 122a, 122b penetrate into tissue that is to be stapled but which is not shown in the Figures. It should be noted that in the particularly advantageous embodiment of the upper die 17 that is illustrated, the holding of the staple 12 on the anvil takes place substantially only in the folding area between the staple cross bar 121 and the staple legs 123a, 123b. This is a considerable simplification compared with the Leukoclip stapling device, in which the upper die consists of several parts, with a central part holding the staple cross bar and lateral parts folding the staple legs.

Because of the arrowhead-shaped design of the ejector element 16, its beveled front edges 163a, 163b interact with the inner and rear surfaces of the staple legs 123a, 123b. As the staple legs 123a, 123b undergo further folding, the entire ejector element 16 is pushed backwards via the beveled planes of the edges 163a, 163b. In the process, as is particularly evident from FIGS. 6 and 7, the elastically resilient area 166 of the ejector element 16 is placed under tension. In the illustrated embodiment, in which the elastically resilient area 166 takes the form of a bending spring, this tensioning of the spring takes place through the elastically resilient area 166 arching upwards perpendicular to the direction of extension of the ejector element 16. While this happens, the pairs of guide fins 164a, 164b and 165a, 165b stabilize the other areas of the ejector element 16 so that its overall movement, and in particular the relevant movement of its arrowhead-shaped front area, is purely linear. A rear housing wall 18 closing off the staple magazine provides a rear stop for the tensioning of the spring.

Once the staple legs 123a, 123b have been fully folded into a position substantially perpendicular to the staple cross bar 121, the staple initially continues to be held on the anvil 14, as before, by the projections 171a, 171b of the upper die 17. In this stage, the front edge 161 of the ejector element 16 is in contact with the rear sides of the staple legs 123a, 123b and applies spring force to the staple 12 in the direction of ejection.

Figure 8:
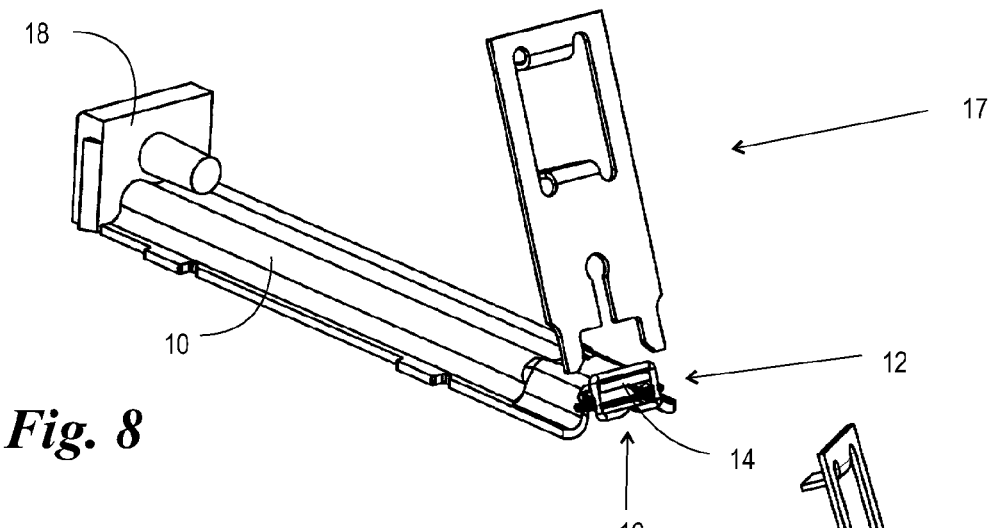
FIG. 8 illustrates a perspective view of the staple ejection area of the stapling device according to one embodiment of the invention in a release position.

FIG. 8 shows the situation that exists when the triggering element, which is not shown, is returned to its ready position, with the upper die 17 being detached from the staple. Correspondingly, the staple ceases to be held on the anvil 14.

Figure 9:
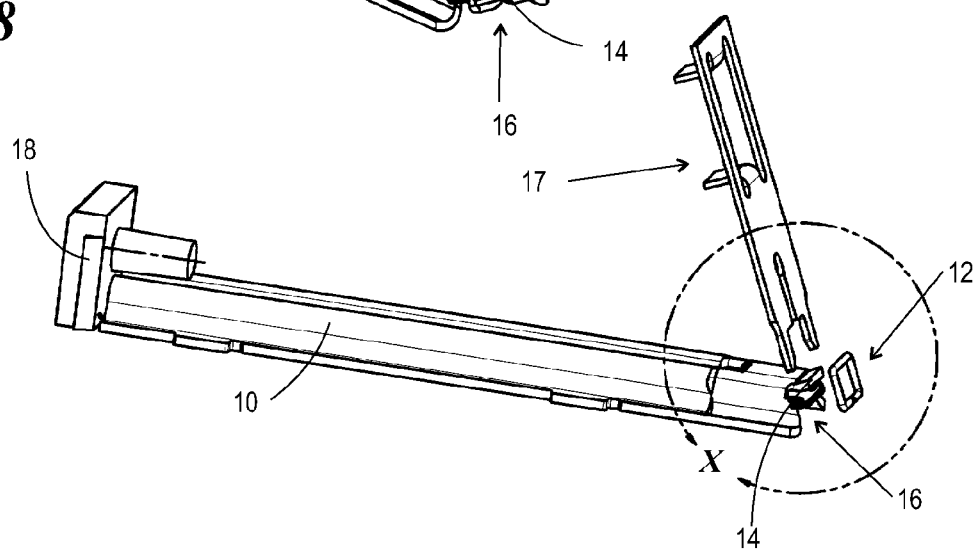
FIG. 9 illustrates a perspective view of the staple ejection area of the stapling device according to one embodiment of the invention, showing the staple being ejected.
Figure 10:
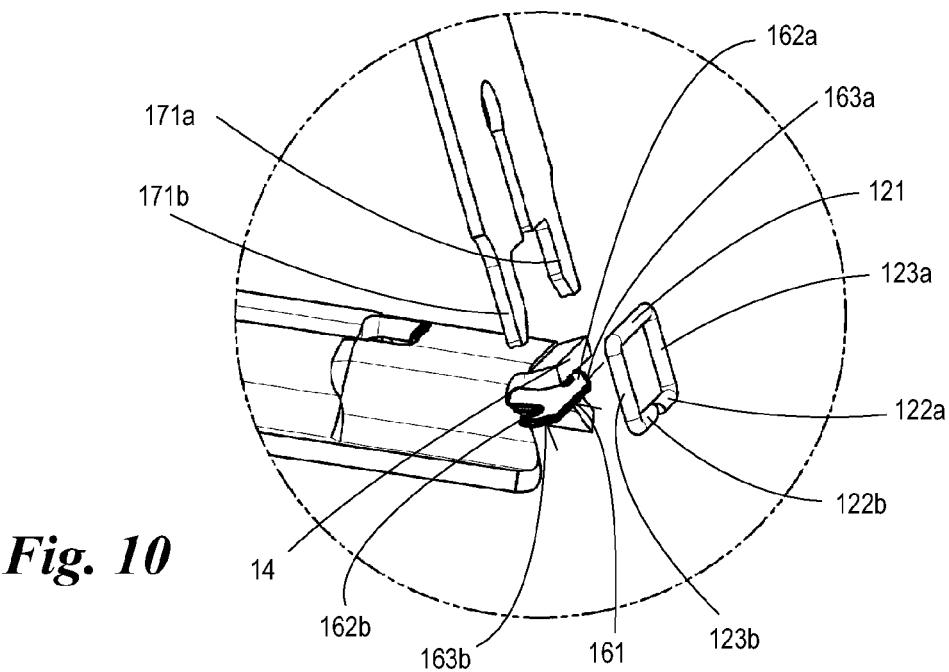
FIG. 10 illustrates an enlarged view of a section of FIG. 9.

As is shown in FIGS. 9 and 10 this release of the staple 12 allows the spring area 166 of the ejector element 16 to relax, as a result of which the front part of said ejector element, guided by the pairs of guide fins 164a, 164b and 165a, 165b, moves linearly forwards and actively pushes the staple 12 from the anvil 14.

In order to restrict the forward linear displacement of the ejector element 16, i.e. in order to prevent the ejector element 16 from slipping out of its guide, a safety projection in the form of an upwards bent tab 167 is formed on the ejector element 16, as can be seen in particular in FIGS. 10 and 11.

Of course, the embodiment discussed in the specific description and shown in the drawings is merely an illustrative example of the invention. The expert in the field has a wide range of possible modifications at his disposal. For example, the arrowhead-shaped configuration of the front area of the ejector element 16 can be differently designed from what is shown. In particular, the flat front edge 161 can be made wider or less wide. What is relevant, however, is the interaction between the beveled arrowhead edges 162a, 162b that cooperate as sloping planes with the inner and rear sides of the staple legs 123a, 123b in order to transform the folding movement of the staple legs 123a, 123b into a linear movement of the ejector element 16 and thus into the tensioning of the spring force, in particular of the elastically resilient area 166. The spring area 166 of the ejector element 16 can also be designed differently from what is shown. For example, as an alternative to, or in addition to an outer tapering, the material can be weakened by producing an elongated cutout so that this area is less stiff than neighbouring areas and can thus be used as a spring element. Alternatively or in addition, a separate spring element may also be used.

What is claimed is:

1. A surgical stapling device for applying staples in a layer of tissue, the surgical stapling device comprising:
    a device body;
    a staple magazine arranged in the device body and adapted to contain a plurality of staples that are stacked in a pre-application position and spring loaded in a staple transport direction towards a staple outlet of the magazine, each of the plurality of staples having a staple cross bar and two staple feet laterally connected and folded substantially perpendicular to the staple cross bar;
    a triggering device transferable between a ready position and an actuation position, the triggering device causing, in response to being transferred from the ready position to the actuation position, an upper die pick up, at the outlet of the staple magazine, a foremost staple of the plurality of staples, and bend, an anvil engaging between the staple feet of and acting as an abutment for the staple cross bar of the foremost staple, each staple foot of the foremost staple inwards into an application position by folding a respective section of the staple cross bar that is adjacent to each respective staple foot of the foremost staple, thus making each respective section into a respective staple leg; and
    an ejector element extending centrally and parallel to the staple transport direction as a flat spring-loaded tongue beneath the anvil, the ejector element being linearly displaceable and being spring-loaded in the direction of staple transport direction, the ejector element being, in it's front section, shaped as an arrowhead comprising two lateral arrowhead wings that each being beveled to the rear of the ejector element, the total front edge of the ejector element having a width that exceeds the distance between the staple legs when the staple legs are in application position,
    wherein the ejector element, in response to the triggering element being transferred from the ready position to the actuating position, is, due to the distance between the bending staple legs narrowing and, thus, the arrowhead wings sliding along the inner rear surfaces of the bending staple legs, displaced opposite to the staple transport direction, thereby increasing spring load, and, when the triggering element is returned to the ready position, said ejector element is, due to the upper die releasing the foremost staple and due to the spring load driving, displaced in the direction of staple transport, thereby kicking off the foremost staple.

2. A stapling device according to claim 1, wherein the ejector element further comprises an elastically resilient area that operates as a pre-tensioned spring to spring load the tongue beneath the anvil.

3. A stapling device according to claim 2, wherein the ejector element comprises a rear section designed as a bending spring that is flexible in a direction perpendicular to the staple transport direction.

4. A stapling device according to claim 1, wherein the device body further comprises a stop operating to limit linear movement of the ejector element in a direction opposite the direction of staple transport.

5. The surgical stapling device according to claim 1,
    wherein the device body further comprises guide recesses, and wherein the ejector element is supported by a plurality of lateral guide fins in a linearly movable manner, the plurality of lateral guide fins engaging corresponding guide recesses.

6. A stapling device according to claim 5, wherein a rear section of the ejector element is designed as a bending spring that is flexible in the direction perpendicular to the staple transport direction, wherein the plurality of lateral guide fins comprises a first pair of lateral guide fins and a second pair of lateral guide fins, wherein the first pair of lateral guide fins is arranged in front of the elastically resilient area of the ejector element and the second pair of lateral guide fins is arranged behind the elastically resilient area of the ejector element.

7. A stapling device according to claim 5, wherein the guide fins are formed with a component perpendicular to the direction of extension of the ejector element.

8. A stapling device according to claim 1, wherein the ejector element has a safety projection that limits movement of the ejector element in the staple transport direction by interacting with a corresponding stop in the device body.

* * * * *